(12) United States Patent
Chang et al.

(10) Patent No.: US 8,569,709 B1
(45) Date of Patent: Oct. 29, 2013

(54) RADIOGRAPHIC IMAGING APPARATUS AND METHODS INCLUDING STABLE POWER DOWN

(75) Inventors: Jeff Hsin Chang, Rochester, NY (US); Gordon Geisbuesch, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 13/488,667

(22) Filed: Jun. 5, 2012

(51) Int. Cl.
  *G01T 1/24* (2006.01)
  *G01T 1/161* (2006.01)
  *F16P 3/14* (2006.01)

(52) U.S. Cl.
  USPC .............. 250/370.14; 250/370.1; 250/363.07; 250/208.4

(58) Field of Classification Search
  USPC ................. 250/370.9, 370.1, 370.14, 363.07, 250/208.4
  See application file for complete search history.

(56) References Cited

U.S. PATENT DOCUMENTS

| | | | |
|---|---|---|---|
| 5,920,070 A * | 7/1999 | Petrick et al. | 250/370.09 |
| 6,399,950 B1 * | 6/2002 | Kimura et al. | 250/370.09 |
| 7,365,337 B2 * | 4/2008 | Tsuchino et al. | 250/370.09 |
| 7,551,428 B2 * | 6/2009 | Homer et al. | 361/679.41 |

* cited by examiner

*Primary Examiner* — David Porta
*Assistant Examiner* — Kenneth J Malkowski (57) ABSTRACT

Embodiments of radiographic imaging systems; radiography detectors and methods for using the same can include radiographic imaging array that can include a plurality of pixels that each include a photoelectric thin-film conversion element coupled to a conversion thin-film switching element. In certain exemplary embodiments, a radiographic imaging array can include a bias control circuit to provide a bias voltage to the photosensors for a portion of the imaging array, an address control circuit to control scan lines, where each of the scan lines is coupled to a plurality of pixels in the portion of the imaging array; and a signal sensing circuit connected to data lines, where each of the data lines is coupled to at least two pixels in the portion of the imaging array, where power of the bias control circuit, the address control circuit, and the signal sensing circuit is not removed simultaneously.

19 Claims, 11 Drawing Sheets

RADIOGRAPHIC IMAGING APPARATUS AND METHODS INCLUDING STABLE POWER DOWN

FIELD OF THE INVENTION

The invention relates generally to the field of radiation conversion apparatus, and in particular to medical radiographic imaging and digital radiographic (DR) detectors, and more particularly to operation procedures for radiographic imaging apparatus comprising non-single crystalline materials.

BACKGROUND

Figure 1:
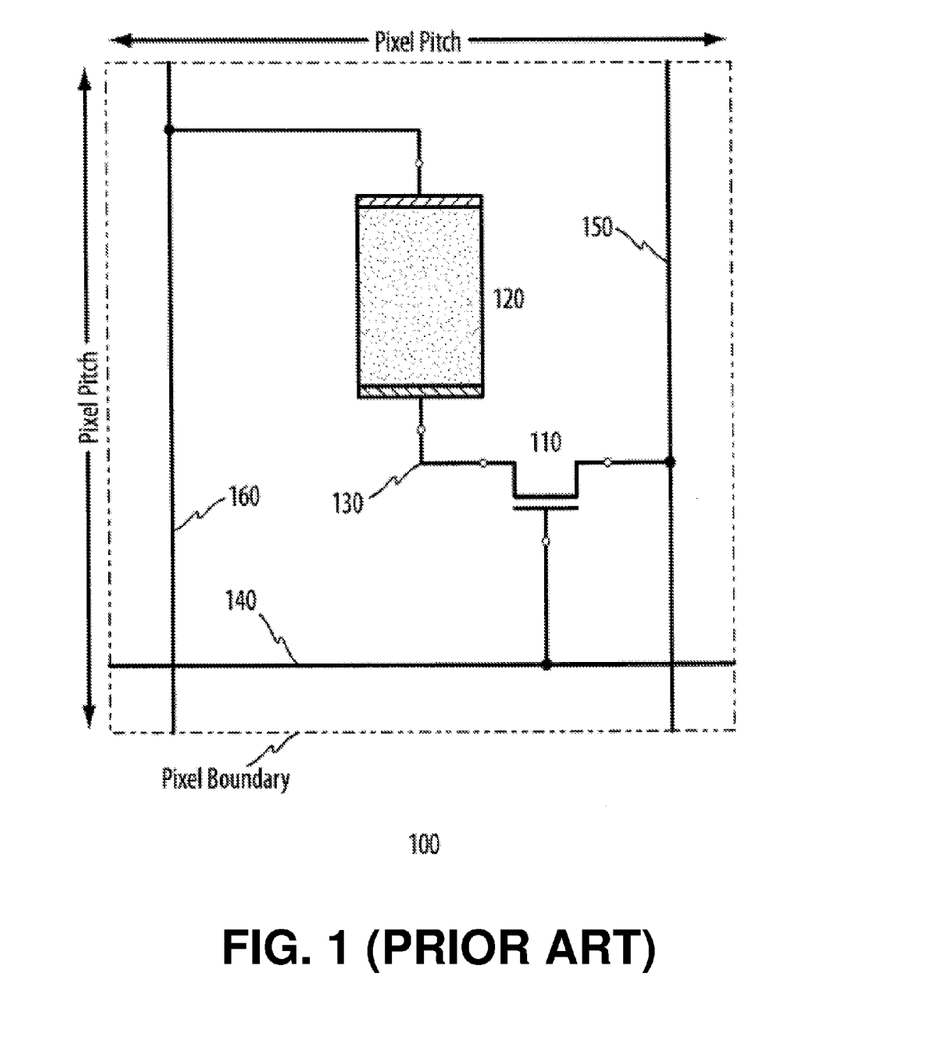
FIG. 1 is a diagram that shows a schematic equivalent circuit for a sensor pixel used in known radiographic imaging arrays.

Imaging arrays comprised of multiple sensor pixels 100 are well known in the imaging art. Sensor pixels 100 typically include a switching element 110 such as a thin-film transistor (TFT), and a photoelectric conversion element 120 such as a photodiode. FIG. 1 shows a schematic equivalent pixel circuit for sensor pixels 100. The photoelectric conversion element 120 or photosensor is sensitive to incident radiation and can generate a number of charge carriers where the number depends on the radiation dosage. In imaging arrays including a plurality of pixels, the photogenerated carriers are usually temporarily stored across the internal capacitance of the sensor or in an on-pixel storage capacitor prior to readout. A task of the switching element 110 is to maintain the signal within the pixel and subsequently enable the readout of the signal from the pixel. A signal of interest can be, for example, represented by the change in charge carriers held at a floating node 130 of the pixel, which is typically manifested as a potential change of floating node 130. Aside from the device elements 110, 120, signal lines are also responsible for the functionality of the sensor pixels 100 and the imaging array. The switching element 110 is controlled by scan line 140 that dictates the time and duration of the signal charge release process. Data line 150 provides a path for the released charge carriers to the readout electronics. Bias line 160 provides the appropriate bias voltages for the photoelectric conversion elements 120.

Figure 2:
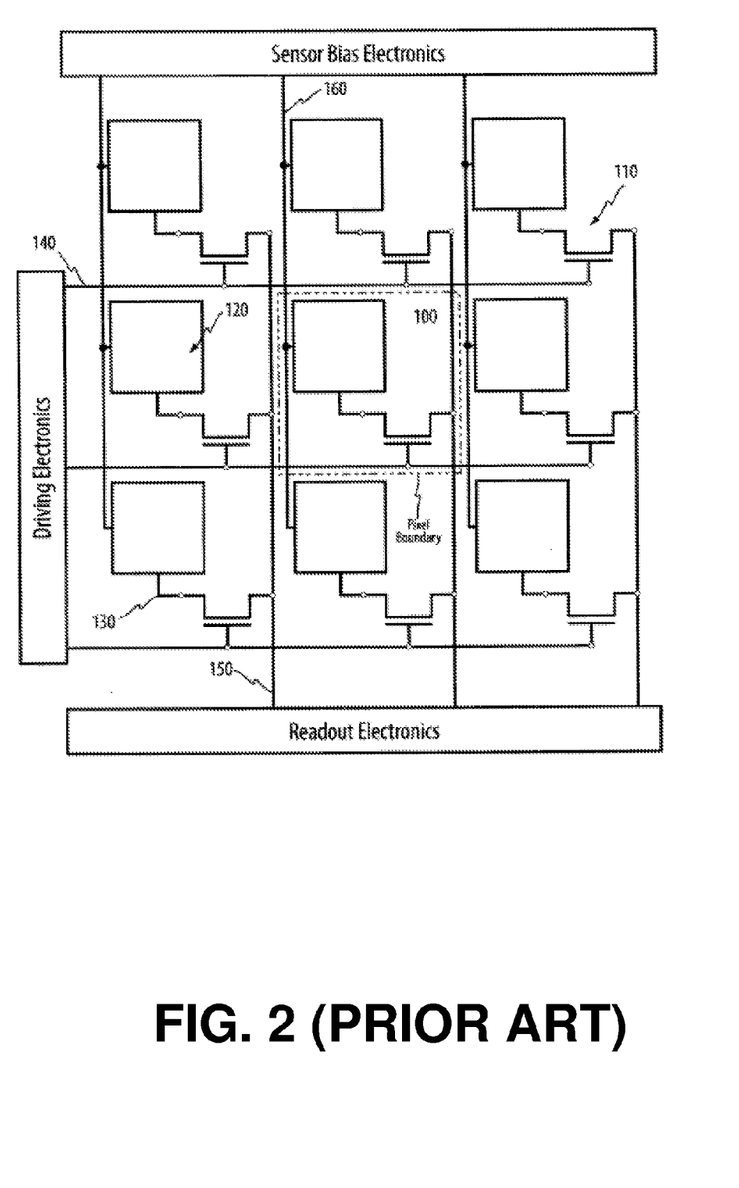
FIG. 2 is a diagram that shows a 3×3 pixel imaging array used for known general radiographic detection devices.

A plurality of sensor pixels can be arranged or tiled in a matrix fashion to form an imaging array. As will be understood to those of ordinary skill in the art, the orientation of the columns and rows is arbitrary, however, for clarity of description it can be assumed that the rows extend horizontally and the columns extend vertically. FIG. 2 shows a schematic equivalent diagram of a 3×3 pixels imaging array that may be used for general radiation detection devices. The bias line 160 is shared among pixels in each column and is coupled to the sensor bias electronics. The data line 150 is shared among pixels in each column and is coupled to the readout electronics. The scan line 140 is shared among pixels in each row and is coupled to the driving electronics. Driving circuitry provides the appropriate signals on scan lines 140 to release the signals stored on the floating nodes 130 of pixels 100 to the data lines 150, for example, one row at a time. The relative waveform timing of the driving electronics, the readout electronics, and the sensor bias electronics may be controlled by an electronic processor (not shown).

For large size imaging arrays, a-Si:H TFT is typically used as the switching element 110. To those of ordinary skill in the art, it is immediately evident that there are numerous other possible choices for the switching elements 110 as well as types of materials that can compose the elements. Due to constraints imposed by the fabrication process of the a-Si:H TFT, there are a number of parasitics associated with the fabricated TFT; these parasitics may sometimes impact the performance of the imaging array and there is a general desire to reduce or minimize their effects.

SUMMARY OF THE INVENTION

An aspect of this application is to advance the art of medical digital radiography.

Another aspect of this application to address in whole or in part, at least the foregoing and other deficiencies in the related art.

It is another aspect of this application to provide in whole or in part, at least the advantages described herein.

An aspect of this application to is to provide methods and/or apparatus to address and/or reduce disadvantages caused by the use of portable (e.g., wireless) digital radiography (DR) detectors and/or radiography imaging apparatus using the same.

An aspect of this application to is to provide radiographic imaging methods and/or apparatus that can shut down (e.g., power-down) a radiographic imaging array in a controlled or uniform state and/or repeatable state.

An aspect of this application to is to provide radiographic imaging methods and/or apparatus that can reset a radiographic imaging array to reduce imaging artifact for subsequent image captures.

An aspect of this application to is to provide radiographic imaging methods and/or apparatus that reduce noise generated in a radiographic imaging array.

In accordance with one embodiment, the present invention can provide a digital radiographic area detector that can include a housing configured to include an upper surface, a lower surface, and side surfaces to connect the upper surface and the lower surface; an insulating substrate inside the housing; an imaging device mounted inside the housing at the insulating substrate, the imaging device comprising a plurality of pixels, each pixel comprising at least one electrically chargeable photosensor and at least one thin-film transistor; a bias control circuit to provide a bias voltage to the photosensors for a portion of the imaging array; an address control circuit to control scan lines, where each of the scan lines is configured to extend in a first direction and is coupled to a plurality of pixels in the portion of the imaging array; and a signal sensing circuit connected to data lines, where each of the data lines is configured to extend in a second direction and is coupled to at least two pixels in the portion of the imaging array; where power of the bias control circuit for the bias line, the address control circuit for the scan lines, and the signal sensing circuit for the data lines is not removed simultaneously.

In accordance with one embodiment, the present invention can provide method of operating a digital radiographic detector, the radiographic detector including an imaging array that can include a plurality of pixels arranged in rows and columns, each pixel including a thin-film photosensor configured to generate a signal based upon radiation received, the method can include operating the imaging array in a first mode, the first mode including providing a first reference voltage using a first reference voltage line to a portion of the imaging array, commanding a multiplexer circuit to selectively couple selected pixels of the portion of the imaging array to enabling scan lines, and reading signals from the selected pixels of the portion of the imaging array using enabled data lines; and operating the imaging array in a second mode, the second mode including sequentially removing power of the first reference voltage, the multiplexer circuit for the scan lines, and the data lines, where the power for the data lines is removed before the power for the first reference voltage that is removed before the power for the multiplexer circuit.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

DESCRIPTION OF EXEMPLARY EMBODIMENTS

The following is a description of exemplary embodiments of the invention, examples of which are illustrated in the accompanying drawings. Wherever possible, the same reference numbers will be used throughout the drawings to refer to the same or like parts.

For simplicity and illustrative purposes, principles of the invention are described herein by referring mainly to exemplary embodiments thereof. However, one of ordinary skill in the art would readily recognize that the same principles are equally applicable to, and can be implemented in, all types of radiographic imaging arrays and that any such variations do not depart from the true spirit and scope of the application. Moreover, in the following description, references are made to the accompanying figures, which illustrate specific exemplary embodiments. Electrical, mechanical, logical and structural changes can be made to the embodiments without departing from the spirit and scope of the invention. In addition, while a feature of the invention can have been disclosed with respect to only one of several implementations/embodiments, such feature can be combined with one or more other features of other implementations/embodiments as can be desired and/or advantageous for any given or identifiable function. The following description is, therefore, not to be taken in a limiting sense and the scope of the invention is defined by the appended claims and their equivalents.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. Where they are used, the terms "first", "second", and so on, do not necessarily denote any ordinal or priority relation, but may be used for more clearly distinguishing one element or time interval from another.

In some exemplary embodiments, a photoelectric conversion element 120 is a hydrogenated amorphous silicon (a-Si:H) n-i-p photodiode and the switching element 110 is a a-Si:H TFT. To those of ordinary skill in the art, it is evident that there are numerous other possible choices for photoelectrical conversion elements 120 and switching elements 110 as well as types of materials that such elements can be composed of.

Figure 3:
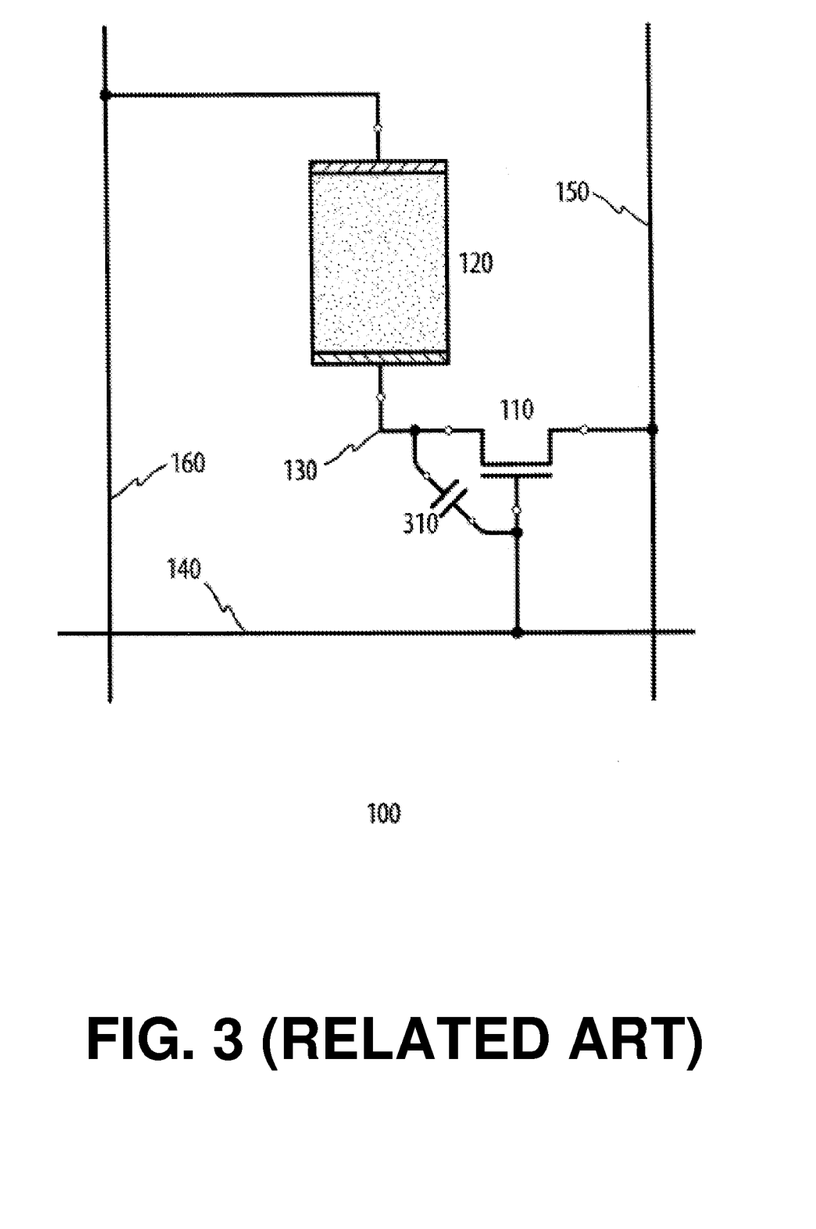
FIG. 3 is a diagram that shows a schematic equivalent circuit for a sensor pixel used in known radiographic imaging arrays showing a parasitic capacitance.

FIG. 3 is a diagram that shows a schematic equivalent pixel circuit for sensor pixels 100 with a parasitic capacitance 310. The shown parasitic capacitance 310 is often referred to as the overlap capacitance of the a-Si:H TFT since the overlap capacitance value is mainly dictated by the overlapping area of the gate electrode of the a-Si:H TFT and other electrodes of the a-Si:H TFT. Since this overlap capacitance couples the scan line 140 signal with the floating node 130 of the pixel 100, during scan line 140 transitions, certain amount of charge is injected into the floating node 130 through this capacitance 310. This process is often referred to as the scan line feed-through process and its existence is well known in the art. The magnitude of this scan line feed-through charge ($Q_{ft}$) can be estimated by $C_{ol} \times \Delta V_{SL}$, where $C_{ol}$ is the magnitude of the overlap capacitance and $\Delta V_{SL}$ is the potential changes of the scan line 140 transitions. Since charge stored in the floating node 130 of the pixel represents the signal charge of the pixel, the feed-through charge introduces unwanted noise charge to the pixel 100.

This scan line feed-through charge phenomenon can be a concern during the power-down process of a radiographic detector where all peripheral electronics of the radiographic imaging array are turned off. The residual charge left in the floating node 130, including the feed-through charge, may cause undesirable effects during the time when the radiographic imaging array is unpowered. Consequently, when powering up the radiographic imaging array again after the radiographic imaging array has been unpowered for a period of time, initial images may show undesirable artifacts.

Figure 4:
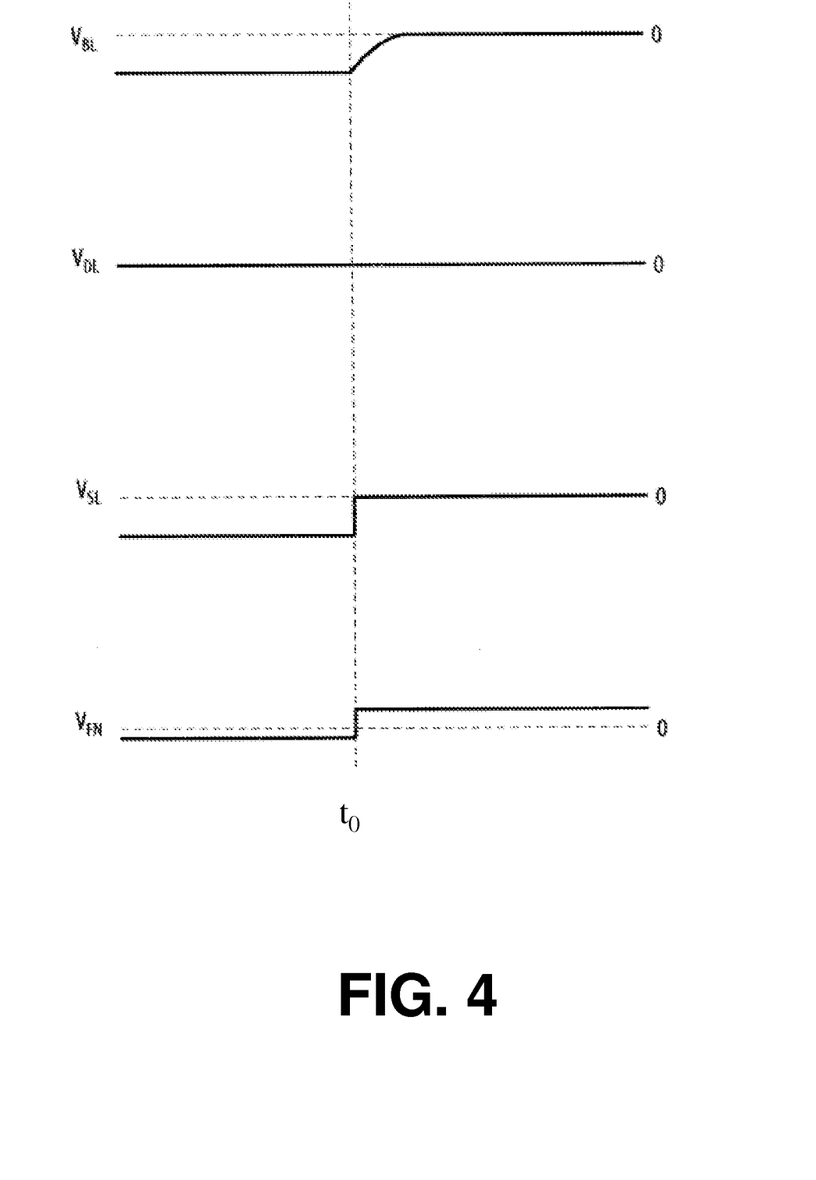
FIG. 4 is a diagram that shows a conceptual timing waveform of a related art power-down operation of a radiographic imaging array.
Figure 5A:
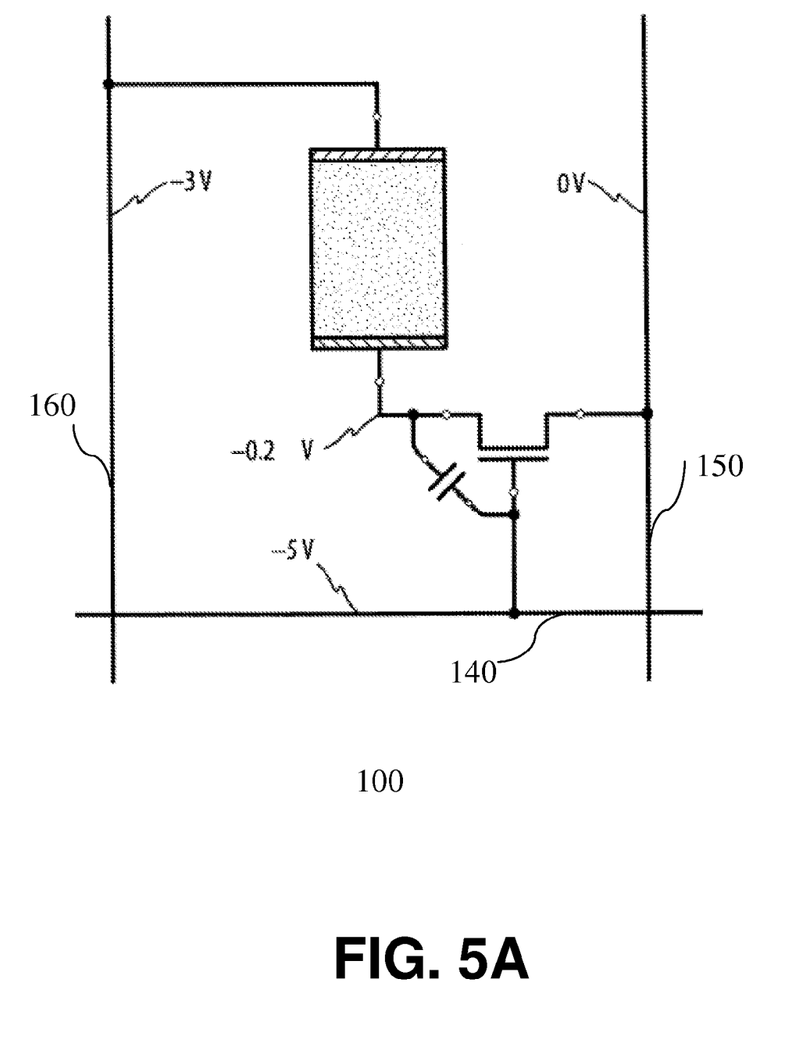
FIGS. 5A-5B are diagrams that respectively show exemplary potentials at each node of a pixel before and after the related art power-down operation of a radiographic imaging array.

Such disadvantages or undesirable effects can be described with an exemplary power-down operation sequence of an imaging array utilizing a-Si:H TFT as the pixel switching element 110 and a-Si:H n-i-p photodiode as the photoelectric conversion element 120. FIG. 4 shows a conceptual timing waveform of an exemplary power-down operation of a radiographic imaging array. The power-down operation commences at time $t_o$ as demarcated on the timing waveform. Prior to $t_o$, the bias line 160 potential ($V_{BL}$) and data line 150 potential ($V_{DL}$) stays fairly constant because the bias line 160 and data line 150 value can dictate the photodiode 120 biases in reset state. During normal imaging operations, the data line 150 and the bias line 160 potential can be set so that the photodiode 120 is reverse biased so that the signal charge collected on the floating node 130 remains there until readout. If the data line 150 and the bias line 160 potential are set so that the photodiode 120 is forward biased during normal imaging operations, signal charge collected at the floating node 130 would bleed or travel to the bias line 160 irrelevant of a state of the switching element 110. For the exemplary case shown in FIG. 4, it is assumed that the cathode of the photodiode is connected to the floating node 130 and a terminal of the switching element 110. Therefore, having a higher data line 150 potential relative to the bias line 160 potential would reverse bias the a-Si:H n-i-p photodiode. Prior to $t_o$, the scan line 140 potential ($V_{SL}$) is set so that the floating node 130 is isolated from the data line 150. The floating node 130 potential ($V_{FN}$) prior to $t_o$ is arbitrarily chosen because the floating node 130 potential prior to $t_o$ represents the charge that can be collected at the floating node 130 from a number of sources prior to power-down. FIG. 5A is a diagram that shows exemplary potentials at each node of a pixel before related art power-down operations (e.g., before $t_o$ such as in FIG. 4) of a radiographic imaging array.

Figure 5B:
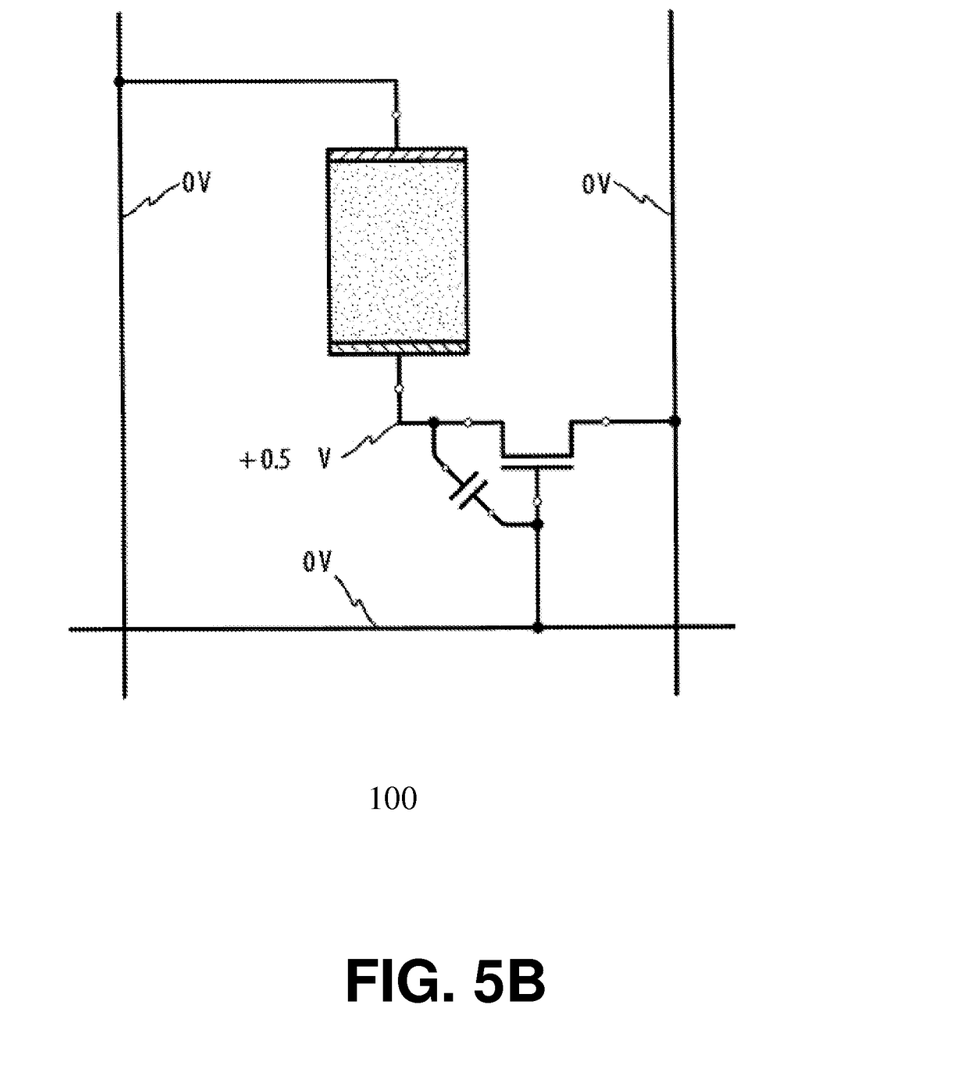

At $t_o$, all driving sources (e.g., driving electronics, readout electronics, and sensor bias electronics) of a radiographic imaging array are powered down, and therefore, the potential seen by the terminals of the imaging array approach the reference potential, 0 V. Since the scan line 140 potential transitions from a negative potential to reference potential, there can be a positive change in the scan line 140 potential; e.g., $\Delta V_{SL}$ is positive. Consequently, $Q_{ft}$ is non-zero and the floating node 130 potential $V_{FN}$ changes about $t_o$ as shown in FIG. 4. At scan line 140 potential of 0 V, the a-Si:H TFT may still be operating in off state, isolating the data line 150 from the floating node 130. FIG. 5B is a diagram that shows exemplary potentials at each node of a pixel after related art power-down operations (e.g., sometime after $t_o$) of a radiographic imaging array. The positive transition on the scan line 140 can bring the floating node 130 potential $V_{FN}$ higher than the bias line 160 potential $V_{BL}$; and consequently, the photodiode 120 can be reverse biased and holding $Q_{ft}$. The value of $Q_{ft}$ can be small relative to the charge capacity of the pixel 100; therefore, the floating node 130 can be reset (e.g., rapidly reset) during the power-up sequence of the radiographic imaging array or radiographic imager. However, the potential change caused by $Q_{ft}$ can affect the trapping behavior of the a-Si:H n-i-p photodiode that takes significantly longer to manifest itself (e.g., several seconds to several minutes). The trapping behavior of the a-Si:H n-i-p photodiode may be one of the causes for the imaging artifact during radiographic imaging array readout and/or can be undesirable.

In view of the issues described above, embodiments of radiographic imaging methods and/or apparatus described herein can provide methods, apparatus or means of shutting down a radiographic imaging array in a selected controlled (e.g., more uniform) state. Additional embodiments of radiographic imaging methods and/or apparatus described herein can provide for resetting radiographic imaging arrays to reduce imaging artifact for subsequent image captures.

Figure 6:
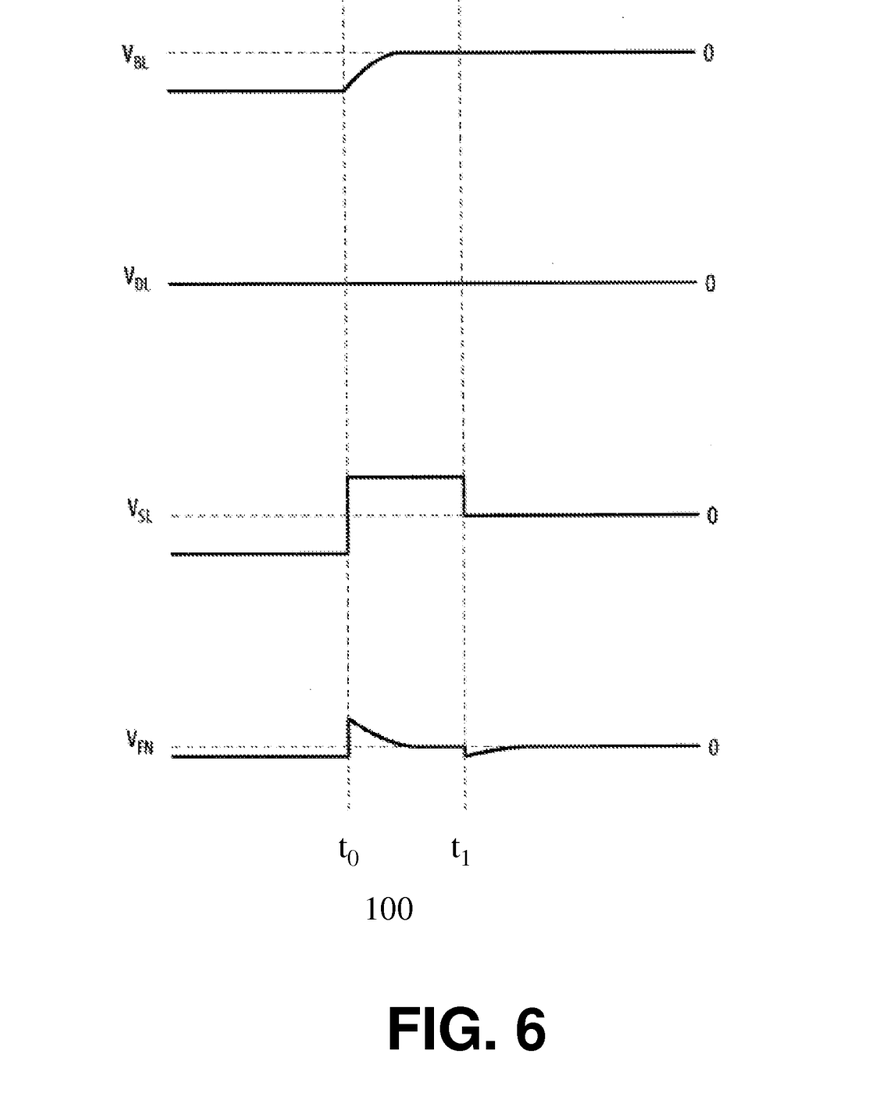
FIG. 6 is a diagram that shows a conceptual timing waveform of an embodiment of power-down operations of a radiographic imaging array according to the application.
Figure 7A:
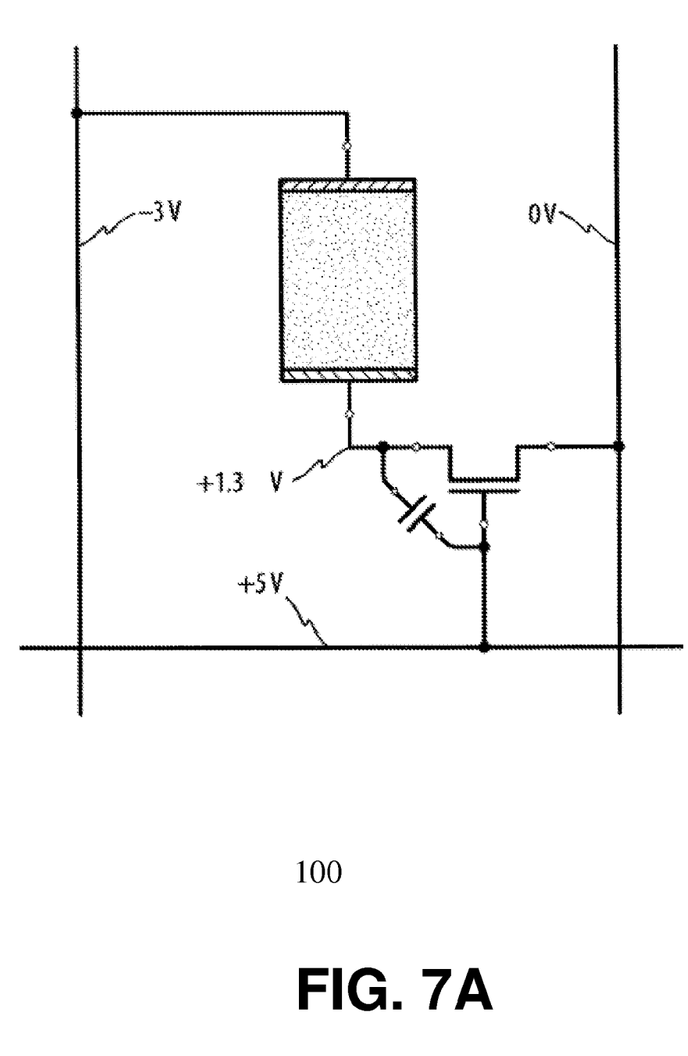
FIGS. 7A-7B are diagrams that respectively show exemplary potentials at each node of a pixel before and after power-down operations as shown in FIG. 6.
Figure 7B:
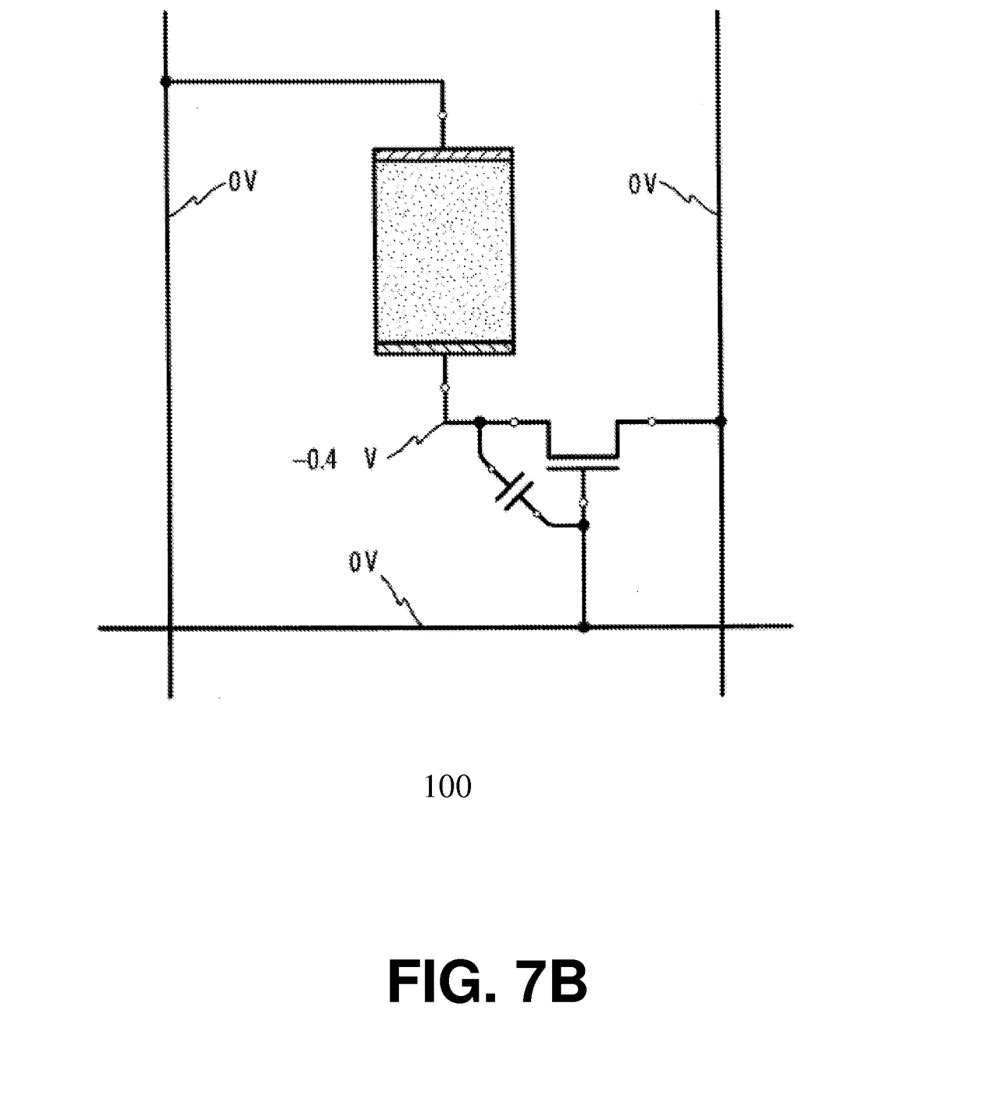

FIG. 6 is a diagram that shows conceptual timing waveform of an embodiment of power-down operations of a radiographic imaging array according to the application. Timing waveforms, as shown in FIG. 6 prior to $t_o$ can be made to be the same as those shown in FIG. 4 for comparison, although other values can be used. The node voltages of the pixel 100 at this stage or just before time $t_o$ shown in FIG. 6 can therefore be shown in FIG. 5A. The scan line 140 at $t_o$ is driven to a positive potential, which can cause a positive transition on the scan line 140 and $\Delta V_{SL}$ can be non-zero (e.g., similar to the case shown in FIG. 4). Consequently, $Q_{ft}$ can be non-zero and the floating node voltage $V_{FN}$ on the floating node 130 can change. For example, since scan line 140 at $t_o$ transitions to a higher value (e.g., compared to the case shown in FIG. 4), $\Delta V_{SL}$ is large and therefore $Q_{ft}$ is larger as well for the case shown in FIG. 6. FIGS. 7A-7B are diagrams that respectively show exemplary potentials at each node of a pixel before and after power-down operations as shown in FIG. 6. Various node potentials after the scan line 140 transition near $t_0$ can be as shown in FIG. 7A. The magnitude of the floating node 130 potential is chosen to show that $Q_{ft}$ is larger for the case of the FIG. 6 embodiment; however, the value itself can be arbitrarily chosen and is inconsequential in describing exemplary embodiments herein. In one embodiment, the scan line voltage $V_{SL}$ is positive but ½× or ¼× of the scan line voltage $V_{SL}$ during normal medical imaging operations. The significantly more positive potential of the scan line 140 can place the a-Si:H TFT in a low impedance mode that can allow carriers to flow to and from the data line 150. Therefore, even though $Q_{ft}$ can be large or larger for the embodiment of FIG. 6 (e.g., compared to the case shown in FIG. 4), the charge (e.g., $V_{FN}$) in the floating node 130 can be drained to the data line 150 over time through the switching element 110. The charge in the floating node 130 can drain as shown in FIG. 6 between time $t_0$ and $t_1$. After the draining of the charge from the floating node 130, the floating node 130 potential $V_{FN}$ can be about the same as the data line 150. Since the biasing circuitry can be powered off at $t_0$, as shown in FIG. 6, the bias line 160 potential can also about the same value as the floating node 130 (e.g., at time $t_1$ or after time $t_0$). Accordingly, at time $t_1$, an approximately zero potential bias can be across the photodiode or photosensor 120.

At $t_1$, the scan line 140 driving circuitry can be powered down and the scan line 140 potential can move to the reference potential (e.g., 0 as shown in FIG. 6). Since scan line 140 can be more positive compared to the reference potential prior to $t_1$, there would be a negative voltage transition at $t_1$. The negative $\Delta V_{SL}$ can cause a negative $Q_{ft}$ feed-through. As shown in FIG. 6, this changes the floating node potential towards a more negative value. Since magnitude of this $\Delta V_{SL}$ is less than the positive change at $t_0$, FIG. 6 representatively illustrates a smaller negative shift in the floating node 130 potential. The scan line 140 potential at $t_1$ can be at the reference potential and can isolate the floating node 130 from the data line 150 similar to the power-down process shown in FIG. 4. However, in contrast to the case shown in FIG. 4, since the floating node 130 potential at $t_1$ is more negative than the bias line 160, the photodiode is forward biased at $t_1$ for the exemplary embodiment shown in FIG. 6. The potentials for each node of the pixel 100 at this point are shown in FIG. 7B. At times following $t_1$, charge (e.g., $V_{FN}$) left on the photodiode floating node 130 can be drained through the forward biased photodiode 120 as shown in FIG. 6.

As shown in FIG. 6, one exemplary power-down sequence embodiment can use both the switching element 110 and the photoelectric conversion element 120 to release unwanted charge from the floating node 130. Further, the bias potential across the photoelectric conversion element 120 can be rendered substantially low after the power-down sequence embodiment. When similar power-down schemes are applied for radiographic imaging arrays, the photodiodes of the pixels in the imaging array can remain in low bias states or a zero bias state. Such low bias states can avoid prolonged bias stress on the photodiode element and/or reduce imaging artifacts when the radiographic detector is powered-up again for image acquisition or normal medical imaging operations.

In one exemplary power-down sequence embodiment, power of a bias control circuit for the bias line 160, power of an address control circuit for the scan lines 140, and power of a signal sensing circuit for the data lines 150 are not removed simultaneously. In contrast, embodiments can sequentially disable the data lines 150, the bias lines 160 and the scan lines 140 so that a conductive path to remove charge from the floating node 130 exists as the radiographic detector is powered down. In one embodiment, conductivity of the photosensors 120 in the imaging array is changed substantially after the power for the address control circuit is removed compared to the conductivity of the photosensors 120 prior to the removal of power for the bias control circuit and the signal sensing circuit. In one embodiment, power for the data line 150 is removed before power to the bias line circuit is removed and then power to the address control circuit is removed. In one embodiment, power for the data line 150 is removed before power to the address control circuit is removed and then power to the bias line circuit is removed. In one embodiment, power to two of the data line sensing circuit, the bias line circuit, and the address control circuit can be removed at (e.g., about) the same time before power is removed from the third of the data line sensing circuit, the bias line circuit, and the address control circuit.

In one embodiment, the detector (e.g., one of the controllers) can set an indicator (e.g., stable shut-down indicator) that the detector was powered down using embodiments of a stable shut-down as variously described herein. Accordingly, upon being powered up for subsequent imaging, the detector having the stable shut-down indicator set, can use a different (e.g., faster) initialization process than when the detector is subsequently powered up with the stable shut-down indicator not set.

In one embodiment, inputs (e.g., voltages) provided at the data lines 150, the scan lines 140 and/or the bias lines 160 can be set to a uniform voltage (e.g., zero volts) to disable pixel and/or drive the floating node 130 charge or voltage closer to zero or steady state. In one embodiment, inputs (e.g., voltages) provided at the data lines 150, the scan lines 140 and/or the bias lines 160 can be set to a uniform charge (e.g., zero charge) to disable pixel and/or drive the floating node 130 charge or voltage closer to zero or steady state.

In one embodiment, the detector can operate in a first mode to detect radiation (e.g., normal imaging operations) and operate in a second mode to disable the detector, where the second mode operates to disable the bias control circuit, the address control circuit, and the signal sensing circuit, where conductivity of photosensors in the detector are reversed in the first mode and the second mode. Further, a conductive path exists to drain charge from a floating node between the photosensors and a readout switch in a pixel when the bias control circuit, the address control circuit, and the signal sensing circuit are disabled (e.g., the second mode).

Embodiments of radiographic imaging systems, radiographic detectors and/or methods for using the same have various advantages. For example, embodiments can provide a more uniform voltage or charge distribution among a plurality of pixels in a radiographic imaging array upon shut-down or power down.

Figure 8:
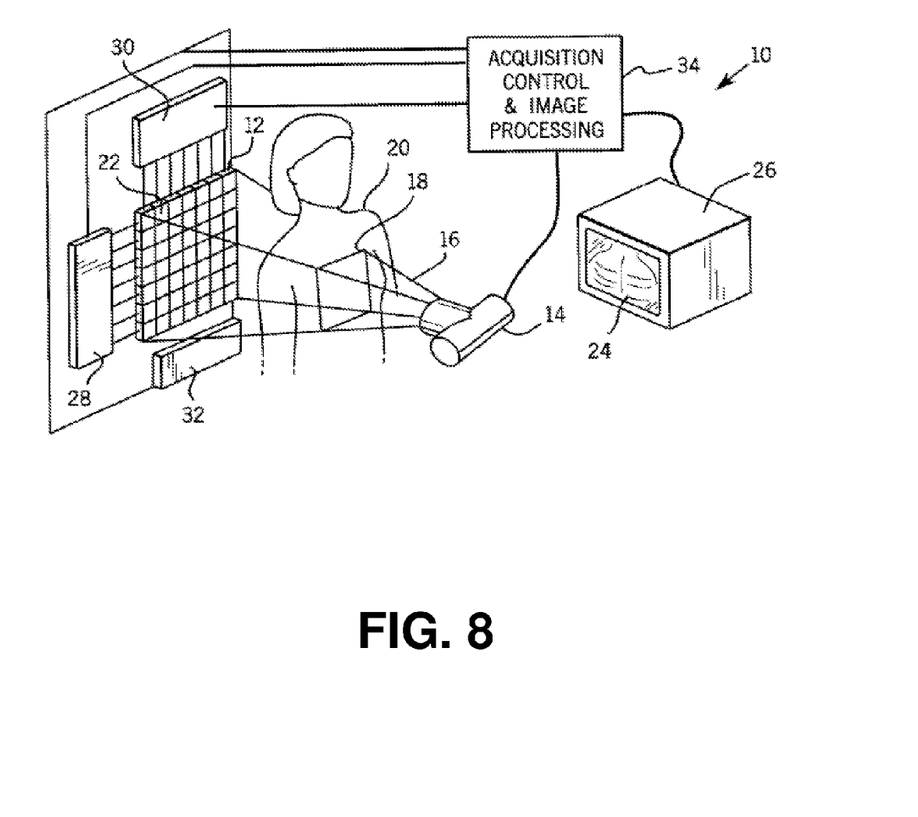
FIG. 8 is a diagram that shows a perspective view of a radiographic imaging apparatus including an area detector according to the application used for a radiographic procedure.

FIG. 8 is a diagram that shows a perspective view of an exemplary radiographic area detector configured to include rows and columns of detector cells in position to receive X-rays passing through a patient during a radiographic procedure. As shown in FIG. 8, an X-ray system 10 that can use an area array 12 can include an X-ray tube 14 collimated to provide an area X-ray beam 16 passing through an area 18 of a patient 20. The beam 16 can be attenuated along its many rays by the internal structure of the patient 20 to then be received by the detector array 12 that can extend generally over a prescribed area (e.g., a plane) perpendicular to the central ray of the X-ray beam 16 (e.g., normal medical imaging operations).

The array 12 can be divided into a plurality of individual cells 22 that can be arranged rectilinearly in columns and rows. As will be understood to those of ordinary skill in the art, the orientation of the columns and rows is arbitrary, however, for clarity of description it will be assumed that the rows extend horizontally and the columns extend vertically.

In exemplary operations, the rows of cells 22 can be scanned one (or more) at a time by scanning circuit 28 so that exposure data from each cell 22 can be read by read-out circuit 30. Each cell 22 can independently measure an intensity of radiation received at its surface and thus the exposure data read-out can provide one pixel of information in an image 24 to be displayed on a display 26 normally viewed by the user. A bias circuit 32 can control a bias voltage to the cells 22.

Each of the bias circuit 32, the scanning circuit 28, and the read-out circuit 30 (e.g., Read Out Integrated Circuits (ROICs)), can communicate with an acquisition control and image processing circuit 34 that can coordinate operations of the circuits 30, 28 and 32, for example, by use of an electronic processor (not shown). The acquisition control and image processing circuit 34, can also control the examination procedure, and the X-ray tube 14, turning it on and off and controlling the tube current and thus the fluence of X-rays in beam 16 and/or the tube voltage and hence the energy of the X-rays in beam 16.

The acquisition control and image processing circuit 34 can provide image data to the display 26, based on the exposure data provided by each cell 22. Alternatively, acquisition control and image processing circuit 34 can manipulate the image data, store raw or processed image data (e.g., at a local or remotely located memory) or export the image data.

Examples of image sensing elements used in image sensing arrays 12 include various types of photoelectric conversion devices (e.g., photosensors) such as photodiodes (P-N or PIN diodes), photo-capacitors (MIS), or photoconductors. Examples of switching elements used for signal read-out include MOS transistors, bipolar transistors, FETs, TFTs or switch components.

In an exemplary hydrogenated amorphous silicon (a-Si:H) based indirect flat panel imager, incident X-ray photons are converted to optical photons, which can be subsequently converted to electron-hole pairs within a-Si:H n-i-p photodiodes. The pixel charge capacity of the photodiodes can be a product of the bias voltage and the photodiode capacitance. In general, a reverse bias voltage is applied to the bias lines to create an electric field (e.g., and hence a depletion region) across the photodiodes and enhance charge collection efficiency. The image signal can be integrated by the photodiodes while the associated TFTs are held in a non-conducting ("off") state, for example, by maintaining the gate lines at a negative voltage. A radiographic imaging array can be read out by sequentially switching rows of the TFTs to a conducting state using TFT gate control circuitry. When a row of pixels is switched to a conducting ("on") state, for example by applying a positive voltage to the corresponding gate line, charge from those pixels can be transferred along data lines and integrated by external charge-sensitive amplifiers. After data is read out, the row can then be switched back to a non-conducting state, and the process is repeated for each row until the entire array has been read out. The signal outputs from the external charge-sensitive amplifiers can be transferred to an analog-to-digital converter (ADC) by a parallel-to-serial multiplexer, subsequently yielding a digital image.

The imaging mode described above applies to static radiographic imaging applications, in which isolated single exposures are obtained. A second operating mode would apply to dynamic imaging applications, in which the radiographic exposure is continuous, such as fluoroscopy. In this operating mode the photodiode reset (a) and the exposure period (b) may be eliminated. The photodiodes are continuously exposed and the charge readout is also performed continuously, with the readout also serving to reset both photodiode and the capacitor.

Figure 9:
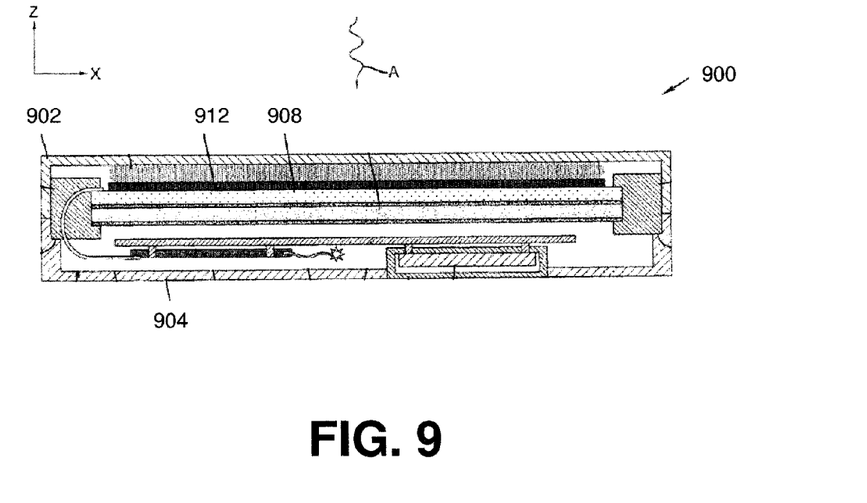
FIG. 9 is a cross-sectional, elevational, diagrammatic view showing a digital radiographic detector.

FIG. 9 shows a cross-sectional view of a DR detector 900 that includes upper housing 902, lower housing 904, secured together and forming a cavity. Mounted within cavity are detector array 908 and screen (scintillator) 912. X-rays are projected to detector 900 in the direction of arrow A.

Although embodiments of the application have been shown with a passive pixel architecture that can include a single photosensor and a single TFT for the DR imaging array, various passive pixel structures can be used including but not limited to 2 TFTs, 3 TFTs, 4 TFTs, 5 TFTs, 6 TFTs, 7 TFTs or more TFTs with at least one photosensor can be used for the pixel described herein.

Embodiments of radiographic imaging systems and/methods described herein contemplate methods and program products on any computer readable media for accomplishing its operations. Certain exemplary embodiments according can be implemented using an existing computer processor, or by a special purpose computer processor incorporated for this or another purpose or by a hardwired system.

Exemplary embodiments herein can be applied to digital radiographic imaging panels that use an array of pixels comprising an X-ray absorbing photoconductor, such as amorphous Selenium (a-Se), and a readout circuit (e.g., direct detectors). Since the X-rays are absorbed in the photoconductor, no separate scintillating screen is required. A scintillating screen is an example of a conversion screen configured to convert first radiation of one or multiple wavelength range into second different radiation of one or multiple wavelength range proximate to a plurality of pixels.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

In certain exemplary embodiments, digital radiographic imaging detectors can include thin-film elements such as but not limited to thin-film photosensors and thin-film transistors. Thin film circuits can be fabricated from deposited thin films on insulating substrates as known to one skilled in the art of radiographic imaging. Exemplary thin film circuits can include amorphous-silicon devices such as a-Si PIN diodes, Schottky diodes, MIS photocapacitors, and be implemented using amorphous semiconductor materials, polycrystalline semiconductor materials such as silicon, or single-crystal silicon-on-glass (SiOG). Certain exemplary embodiments herein can be applied to digital radiographic imaging arrays where switching elements include thin-film devices including at least one semiconductor layer. Certain exemplary embodiments herein can be applied to digital radiographic imaging arrays where the DR detector is a flat panel detector, a curved detector or a detector including a flexible imaging substrate.

The array 12 can be divided into a plurality of individual cells 22 that can be arranged rectilinearly in columns and rows. As will be understood to those of ordinary skill in the art, the orientation of the columns and rows is arbitrary, however, for clarity of description it will be assumed that the rows extend horizontally and the columns extend vertically.

Consistent with exemplary embodiments, a computer program with stored instructions that perform on image data accessed from an electronic memory can be used. As can be appreciated by those skilled in the image processing arts, a computer program implementing embodiments herein can be utilized by a suitable, general-purpose computer system, such as a personal computer or workstation. However, many other types of computer systems can be used to execute computer programs implementing embodiments, including networked processors. Computer program for performing method embodiments or apparatus embodiments may be stored in various known computer readable storage medium (e.g., disc, tape, solid state electronic storage devices or any other physical device or medium employed to store a computer program), which can be directly or indirectly connected to the image processor by way of the internet or other communication medium. Those skilled in the art will readily recognize that the equivalent of such a computer program product may also be constructed in hardware. Computer-accessible storage or memory can be volatile, non-volatile, or a hybrid combination of volatile and non-volatile types.

It will be understood that computer program products implementing embodiments of this application may make use of various image manipulation algorithms and processes that are well known. It will be further understood that computer program products implementing embodiments of this application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with computer program product implementing embodiments of this application, are not specifically shown or described herein and may be selected from such algorithms, systems, hardware, components and elements known in the art.

While the invention has been illustrated with respect to one or more implementations, alterations and/or modifications can be made to the illustrated examples without departing from the spirit and scope of the appended claims. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only. The scope of the invention is indicated by the appended claims, and all changes that come within the meaning and range of equivalents thereof are intended to be embraced therein.

What is claimed is:

1. A digital radiographic area detector comprising:
   an insulating substrate;
   an imaging device mounted to the insulating substrate, the
      imaging device comprising a plurality of pixels, each pixel comprising at least one electrically chargeable photosensor and at least one thin-film transistor;

a bias control circuit to provide a bias voltage to the photosensors for a portion of the imaging array;

an address control circuit to control scan lines, where each of the scan lines is configured to extend in a first direction and is coupled to a plurality of pixels in the portion of the imaging array; and a signal sensing circuit connected to data lines, where each of the data lines is configured to extend in a second direction and is coupled to at least two pixels in the portion of the imaging array;

where power supplied to the bias control circuit for the bias line, power supplied to the address control circuit for the scan lines, and power supplied to the signal sensing circuit for the data lines are not removed simultaneously, the imagining device to operate in a first mode to detect radiation, the imaging device to remove power from the bias control circuit, the address control circuit, and the signal sensing circuit in a second mode, where conductivity of the photosensor is reversed in the first mode and the second mode.

2. The digital radiographic area detector of claim 1, where the power for the bias line circuit is removed before the power to the address control circuit is removed.

3. The digital radiographic area detector of claim 1, where conductivity of the photosensors in the portion of the imaging array is changed after the power for the address control circuit is removed compared to the conductivity of the photosensors before the power for the bias control circuit, the address control circuit, and the signal sensing circuit is removed.

4. The digital radiographic area detector of claim 3, where the photosensor is a photodiode that is forward biased after the power for the address control circuit is removed.

5. The digital radiographic area detector of claim 1, where the photosensor is a photodiode that is forward biased after the power for the address control circuit is removed.

6. The digital radiographic area detector of claim 1, where the photosensor includes at least one semiconductor layer, and that at least one semiconducting layer comprises amorphous silicon, micro-crystalline silicon, poly-crystalline silicon, organic semiconductor, and metal oxide semiconductors.

7. The digital radiographic area detector of claim 1, where the thin-film transistor includes at least one semiconductor layer, and the at least one semiconducting layer comprises amorphous silicon, micro-crystalline silicon, poly-crystalline silicon, organic semiconductor, and metal oxide semiconductors.

8. The digital radiographic area detector of claim 1, where a signal storage element comprises at least one dielectric layer, and that at least one dielectric layer comprises amorphous silicon, micro crystalline silicon, poly-crystalline silicon, organic semiconductor, and metal oxide semiconductors.

9. The digital radiographic area detector of claim 1, where the signal sensing circuits comprise at least one of an analog to digital conversion circuit, an analog amplifier, a charge to voltage conversion circuit, a current to voltage conversion circuit, an analog multiplexer, a digital multiplexer, a data communication circuit, or semiconductor integrated circuits attached to the data lines.

10. The digital radiographic area detector of claim 1, comprising:
a conversion screen configured to convert first radiation of one or multiple wavelength range into second different radiation of one or multiple wavelength range proximate to the plurality of pixels.

11. The digital radiographic area detector of claim 1, comprising:
a radiation source for generating radiation.

12. The digital radiographic area detector of claim 1, wherein the DR detector is a flat panel detector, a curved detector or a detector including a flexible imaging substrate, and
where the digital radiographic area detector is a portable detector or battery powered.

13. A method of operating a digital radiographic detector, the radiographic detector including an imaging array comprising a plurality of pixels arranged in rows and columns, each pixel comprising a thin-film photosensor configured to generate a signal based upon radiation received, the method comprising:
operating the imaging array in a first mode, the first mode comprising,
providing a first reference voltage using a first reference voltage line to a portion of the imaging array,
commanding a multiplexer circuit to selectively couple selected pixels of the portion of the imaging array to enabling first control lines, and
reading signals from the selected pixels of the portion of the imaging array using enabled second control lines; and
operating the imaging array in a second mode, the second mode comprising,
sequentially removing power of the first reference voltage, the multiplexer circuit for the first control lines, and the second control lines, where the power for the second control lines is removed before the power for the first reference voltage; and the power for the first reference voltage is removed before the power for the multiplexer circuit.

14. The method of claim 13, where in the second mode, the pixels in the imaging array reach an increased uniformity low charge state upon removal of the power for the multiplexer circuit.

15. The method of claim 13, where in the second mode, the pixels in the imaging array comprise a photosensor is a photodiode that is biased toward the first reference voltage line after the power for the multiplexer circuit is removed.

16. The method of claim 13, where the radiographic detector further comprises:
at least one indirect imaging array comprising:
a plurality of pixel cells, where a scan line and a data line are common to more than one pixel cell,
driving circuits coupled to a plurality of rows of the imaging array,
readout circuits coupled to a plurality of columns of the imaging array, and
where the first reference voltage line to connect the first reference voltage to a first terminal of a plurality of photosensors in the portion of the imaging array; and
a conversion screen configured to convert first radiation of one or multiple wavelength range into second different radiation of one or multiple wavelength range proximate to the plurality of pixel cells.

17. The method of claim 13, where in the sequentially removing power comprises providing uniform zero voltage or charge inputs to the first reference voltage, the first control lines, and the second control lines.

18. The method of claim 13, further comprising setting a first indicator being a stable shut down indicator to a first high value, and clearing the first indicator to a second low value upon restarting the detector.

19. A digital radiographic area detector comprising:
- a housing configured to include an upper surface, a lower surface, and side surfaces to connect the upper surface and the lower surface;
- an insulating substrate inside the housing;
- an imaging device mounted inside the housing on the insulating substrate, the imaging device comprising a plurality of pixels, each pixel comprising at least one electrically chargeable photosensor and at least one thin-film transistor;
- a bias control circuit to provide a bias voltage to the photosensors for a portion of the imaging array;
- an address control circuit to control scan lines, where each of the scan lines is configured to extend in a first direction and is coupled to a plurality of pixels in the portion of the imaging array; and
- a signal sensing circuit connected to data lines, where each of the data lines is configured to extend in a second direction and is coupled to at least two pixels in the portion of the imaging array;
- the imaging device to operate in a first mode to detect radiation, the imaging device to operate in a second mode for power down operations of the imaging device by removing power from the bias control circuit, power from the address control circuit, and power from the signal sensing circuit,
- where in the second mode, the power of a first one of the bias control circuit, the address control circuit, and the signal sensing circuit is removed before the power of a second one of the bias control circuit, the address control circuit, and the signal sensing circuit, and then the power of the second one of the bias control circuit, the address control circuit, and the signal sensing circuit is removed before the power of the remaining one of the bias control circuit, the address control circuit, and the signal sensing circuit is removed.

* * * * *